(12) United States Patent
Blumke et al.

(10) Patent No.: US 7,043,963 B2
(45) Date of Patent: May 16, 2006

(54) APPARATUS AND METHOD FOR DETERMINING EVAPORATIVE EMISSIONS

(75) Inventors: Dennis M Blumke, Washington, MI (US); Ron Berndt, Beverly Hills, MI (US); Amin Haj-Ali, Dearborn Heights, MI (US)

(73) Assignee: DaimlerChrysler Corporation, Auburn Hills, MI (US)

( * ) Notice: Subject to any disclaimer, the term of this patent is extended or adjusted under 35 U.S.C. 154(b) by 76 days.

(21) Appl. No.: 10/886,115

(22) Filed: Jul. 7, 2004

(65) Prior Publication Data

US 2006/0005607 A1    Jan. 12, 2006

(51) Int. Cl.
   *G01M 3/02*     (2006.01)
(52) U.S. Cl. ............................................. 73/37; 73/1.06
(58) Field of Classification Search .................... 73/37, 73/23.31, 25.01, 23.2, 1.02, 1.06
   See application file for complete search history.

(56) References Cited

U.S. PATENT DOCUMENTS

| 5,526,675 A | * | 6/1996 | Ratton ........................ 73/23.2 |
| 5,592,372 A | * | 1/1997 | Artail et al. ................... 700/73 |
| 6,405,745 B1 | * | 6/2002 | Kar et al. ....................... 137/2 |
| 6,575,012 B1 | * | 6/2003 | Aronsson et al. .......... 73/23.31 |
| 6,865,926 B1 | * | 3/2005 | O'Brien et al. ............ 73/23.27 |

* cited by examiner

*Primary Examiner*—Charles Garber
(74) *Attorney, Agent, or Firm*—Ralph E. Smith

(57) ABSTRACT

A sealed housing evaporative determination (SHED) apparatus and method for practically zero emission vehicles (PZEV) provides periodic sampling of ambient air within a substantially air-tight testing structure enclosing a vehicle under test. Pressure drops within the testing structure are compensated by injecting air substantially free of hydrocarbons into the testing structure. Pressure increases within the testing structure are reduced by withdrawing ambient air from the testing structure. Hydrocarbon content of any withdrawn ambient air is determined from the latest sample, and cumulative evaporative emissions are adjusted accordingly.

14 Claims, 3 Drawing Sheets

APPARATUS AND METHOD FOR DETERMINING EVAPORATIVE EMISSIONS

BACKGROUND OF THE INVENTION

The present invention relates generally to motor vehicle emissions testing and, more particularly, to a computer controlled sealed housing evaporative determination (SHED) testing apparatus and method for automatically testing motor vehicle evaporative emissions for practically zero emission vehicles (PZEV) under a number of testing schedules.

In addition to commonly known tailpipe exhaust emissions produced during engine operation, there are also evaporative emissions which are generated while the vehicle is simply sitting parked. Testing for evaporative emissions is typically conducted according to what is commonly known as a sealed housing evaporative determination (SHED) test.

Modern regulations require measuring evaporative emissions produced by a vehicle over the course of several days and in response to changing temperature conditions. However, changes in air temperature cause corresponding changes in the volume and hence changes in the pressure of the ambient air within the SHED structure. Pressure differences between the interior and the ambient air of the SHED structure and the outside environment encourage migration of air either into or out of the testing structure through any leaks, thus affecting the accuracy of the test results. Therefore, it is desirable to control the pressure changes in order to maintain a pressure difference between the interior of the SHED structure and the surrounding outside atmosphere as near zero as possible.

One known approach to performing variable temperature SHED tests while controlling the pressure differential is set forth in U.S. Pat. No. 5,592,372. While the apparatus and methods disclosed by the '372 patent are suitable for emission testing on standard vehicles, new approaches are now required for PZEV testing, because the levels of hydrocarbons being monitored are much lower than those of standard vehicles. PZEV testing additionally requires a breakdown of the components of the hydrocarbons being emitted to determine the source of the emissions—e.g. refrigerant from the air conditioning system versus fuel vapor from the fueling system.

Hence, there is seen to be a need for SHED testing of PZEV's wherein the evaporative emission levels being monitored are substantially lower than for standard vehicles tested under previous arrangements.

SUMMARY OF THE INVENTION

In accordance with one aspect of the invention, a system for testing motor vehicle evaporative emissions includes a substantially air-tight testing structure adapted for enclosing a motor vehicle under test, the testing structure containing a known volume of ambient interior air. A sampling mechanism for periodically measuring and analyzing component parts of hydrocarbons in a sample of the ambient interior air is coupled to the testing structure. A pressure measuring mechanism for indicating a pressure differential between the ambient interior air of the testing structure and atmosphere outside of the testing structure is operative to enable an injector element to inject air containing substantially zero hydrocarbons into the testing structure whenever the pressure of the atmosphere outside of the testing structure is higher than the pressure of the ambient interior air by a preselected differential. The pressure measuring mechanism is likewise operative to enable an exhaling element to withdraw interior ambient air from the testing structure whenever the pressure of the ambient air interior to the structure is higher than the pressure of the atmosphere outside of the structure by a predetermined differential. A flow measuring and calculating element determines in conjunction with a most recent sample from the sampling mechanism an amount of hydrocarbon exhaled from the testing structure whenever the exhaling element is withdrawing interior ambient air from the testing structure.

In another aspect of the invention, a method for determining evaporative emissions of a motor vehicle over a predetermined test time interval includes enclosing a subject motor vehicle in a substantially air-tight testing structure containing a known volume of ambient interior air, periodically sampling during the test time interval the ambient interior air for hydrocarbon content and maintaining a running count of the hydrocarbon content. A pressure differential between the ambient interior air and atmosphere outside of the testing structure is monitored, and air containing substantially zero hydrocarbons is injected into the testing structure whenever the pressure differential indicates atmospheric pressure outside the testing structure exceeds internal ambient air pressure by a preselected amount. Interior ambient air from the testing structure is withdrawn therefrom whenever the pressure differential indicates internal ambient air pressure exceeds atmospheric pressure outside the testing structure by a preselected amount. An amount of hydrocarbons withdrawn from the testing structure is determined for any given sample and the running count of the hydrocarbons emitted is adjusted accordingly.

BRIEF DESCRIPTION OF THE DRAWING

The objects and features of the invention will become apparent from a reading of a detailed description, taken in conjunction with the drawing, in which.

DETAILED DESCRIPTION

Figure 1:
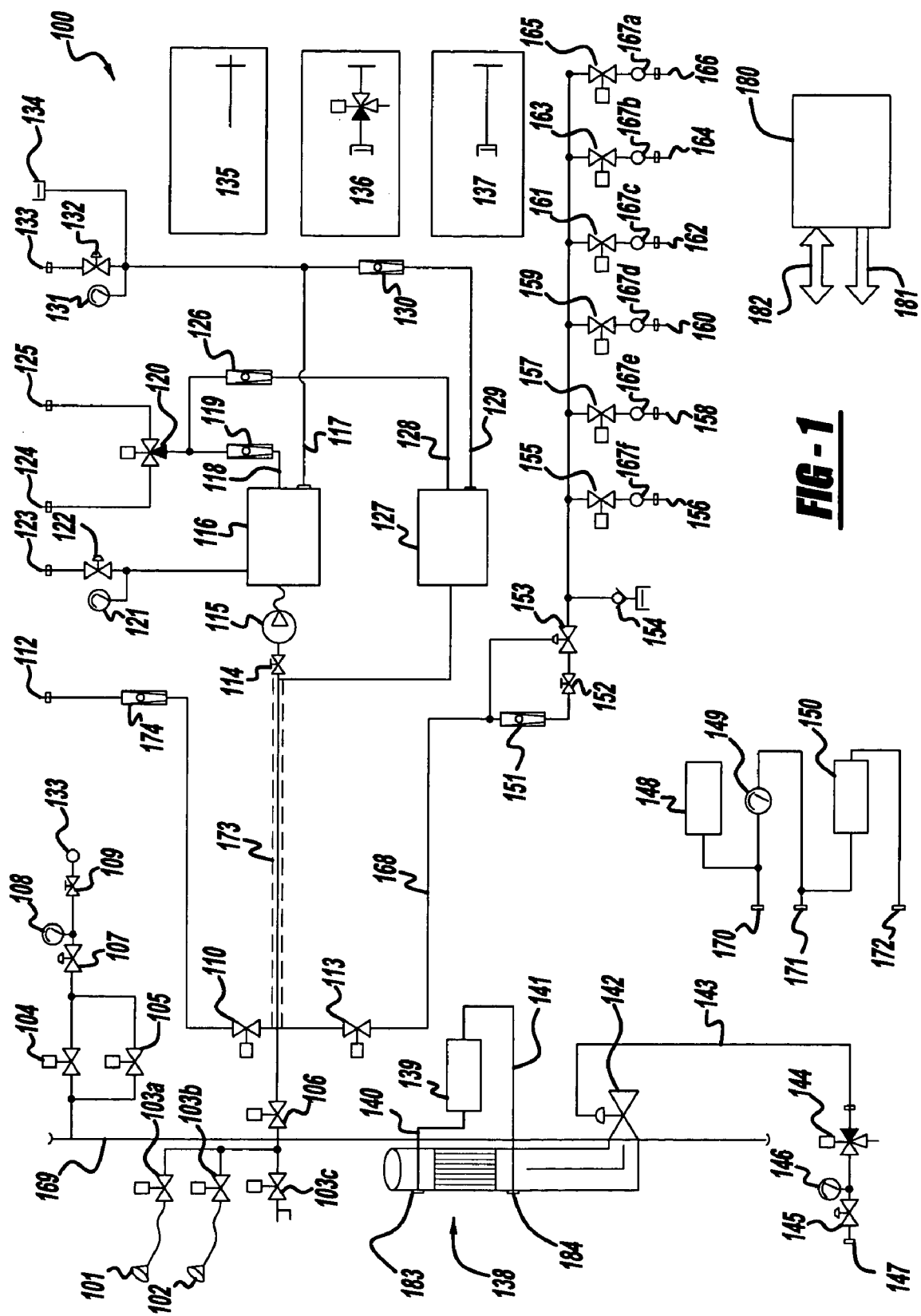
FIG. 1 is a block diagram of a sampling and calibration system for SHED testing arranged in accordance with the principles of the invention.

FIG. 1 sets forth the block diagram of an arrangement for use with a substantially air-tight testing structure for monitoring evaporative emissions from vehicles while in a non-running condition. The vehicle under test (not shown) is placed within the testing structure having a wall 169 through which periodic air sampling is performed.

A heated air sampling line or conduit 173 extends via valve 106 through testing structure wall 169 and then through another control valve 103c to a sampling probe for inside ambient air of the testing structure. Additional specific locations associated with the vehicle under test may be sampled via probes 102 and 101 respectively coupled to the sampling conduit via control valves 103b and 103a.

A source 133 of substantially zero hydrocarbon containing air is coupled to the interior of the testing structure via wall 169 through regulator valve 107, ball valve 109 and control valves 104 and 105. The pressure of this zero HC air is monitored via gauge 108. As will be explained in more detail below, zero hydrocarbon air is introduced into the testing structure via wall 169 whenever inside ambient air has been bled off to bring the pressure differential between the outside atmosphere and the interior of the testing structure substantially to zero.

Heated sampling conduit 173 terminates at a micro-metering needle valve 114 and a bellows pump 115, in turn coupled to a flame ionization detector (FID) 116 which measures the total hydrocarbon content of a sample. Heated conduit 173 additionally is coupled to a gas analyzer 127 for analysis of the specific types of hydrocarbons present in the sample. Analyzer 127 preferably comprises an Innova model 3433 photoacoustic gas analyzer.

FID 116 is coupled to a fuel source 123 via a regulator valve 122 and the pressure in the fuel line is monitored by gauge 121. Additionally, FID 116 is coupled via path 118 to a flow meter 119 and then via valve 120 to a Return-to-SHED line 124 and a dump 125.

Analyzer 127 is coupled via path 128 and flow meter 126 to control valve 120 for access to dump 125 or RTS 124. An air input 129 of analyzer 127 feeds a source of zero hydrocarbon air 133 via regulator 132 and flow meter 130 to analyzer 127 for providing purge air thereto. A front panel access air source 134 is also provided for diagnostic purposes. Zero hydrocarbon air is input to FID 116 via path 117 for enabling the combustion process of the flame of FID 116.

Arrangement 100 advantageously utilizes a spill-over cal-through sampling system. A sample is taken every predetermined period, for example ten minutes, and the hydrocarbon content of emissions within testing structure defined by wall 169 is then periodically updated. FID 116 is likewise periodically calibrated via a spill-over arrangement comprising conduit 168 flowing through a control valve 113 past an end of heated conduit 173, then through control valve 110 and flow meter 174 to dump 112. A preselected level of hydrocarbon content is derived from various supplies of propane for calibration purposes. These supplies 156, 158, 160, 162, and 164 respectively provide propane with known levels of hydrocarbon content for the calibration procedure. Additionally, a source of zero hydrocarbon air 166 is made available to the calibration spillover pathway. The calibration gas sources are controlled via solenoid valves 155, 157, 159, 161, 163 and 165. The calibration source then proceeds through regulator valve 153 and control valve 152 through a flow meter 151 to path 168. Control valves 110 and 113 are closed during the normal sampling routine but are open for the calibration. Valve 106 would then be closed during calibration. Back-flow and contamination of the calibration gas sources are prevented via check valves 167a–f associated respectively with the zero hydrocarbon air source 165 and propane sources control valves 163, 161, 159,157 and 155.

The pressure differential between the outside atmosphere and the inside ambient air of the testing structure is determined by a Dwyer magnahelic water column gauge 149 with an electrical output which is utilized to actuate valve 142 to enable the testing structure to "exhale" so as to bring the pressure differential down substantially to zero. Barometer 148 also monitors ambient atmosphere external to the testing structure and pressure transducer 150 is used to monitor pressure of fuel tank 172.

The volume of interior ambient air which is exhaled via ball valve 142 is determined using a laminar flow element 138 with pressure probes 183 and 184 at opposite ends thereof. The pressure differential across the laminar flow element is then monitored via pressure transducer 139 coupled via leads 140 and 141 to probes 183 and 184. A processor based controller 180 is coupled to the various elements of FIG. 1 via a data distribution and collection bus 182 and via a control bus 181. When the amount of exhaled air is to be determined by controller 180, the controller 180 uses transducer 139 to determine the pressure differential across the laminar flow element 138 which in turn enables the computer to derive the flow rate at the time of exhale. The hydrocarbon content in the ambient air sample from the latest sample times the volume of air exhaled is used to derive the hydrocarbon content of the air which was exhaled. This amount is then used to adjust the running total being maintained at controller 180.

When a predetermined unacceptable pressure differential is detected by gauge 149, valve 144 is opened and shop air at supply 147 via regulator valve 145 is directed to ball valve 142 to open same for enabling air to exit from the interior of the testing structure via wall 169.

Blocks 135, 136 and 137 of FIG. 1 set forth three alternative approaches to performing "retention testing" of the test structure, which basically is a measurement of the air tightness of that structure. In a retention test, a known quantity of propane is introduced into the sealed test structure. After a cycle time, for example, twenty-four hours, the introduced hydrocarbons are measured and a preordained amount of hydrocarbon must remain within the testing structure for it to be certified. The known amount of hydrocarbons is introduced via one of the three approaches set forth in blocks 135, 136, and 137. Blocks 135 and 137 present alternate approaches to gravimetric propane injection for retention testing—a preferred injection method for this invention. A gravimetric hydrocarbon injection device is basically a small cylinder hooked up to pure propane and coupled to a hole in the side of the wall 169. Once the propane is injected, the cylinder is weighed to determine precisely how much propane was injected. Block 135 injects gravimetrically via a manually operated valve, while block 137 utilizes a quick-connect coupling. Of course, the injection hole is capped when not in use.

Alternatively, to gravimetric coupling, one could use a critical flow orifice in wall 169, as represented by block 136.

An advantage of the previously discussed periodic calibration of FID 116 is that, since the calibration gas from sources 156, 158, 160,162, 164 or 166 is introduced past an end of conduit 173, the calibration gas also flows through heated conduit 173. Therefore, any contamination in sample conduit 173 or the valves associated therewith is taken into account when calibrating FID 116.

An additional improvement attained with the invention is the use of substantially zero hydrocarbon air as an "inhale" source whenever the pressure of the outside atmosphere exceeds that of the interior ambient air of the testing structure by a predetermined margin. Introducing zero hydrocarbon air enables the evaporation monitoring to proceed without the necessity of altering the running count of hydrocarbons within the testing structure when such air is introduced to overcome the unacceptable pressure difference.

As with prior approaches to evaporative emission monitoring, FID 116 is used to determine total hydrocarbon content of any given sample. An advantage of this invention is the addition of the gas analyzer 127 which is capable of determining up to six different specific types of hydrocarbons in the sample being emitted. This helps determine which vehicle systems are contributing to the evaporative emissions. For example, with the use of analyzer 127, one can test a flexible fuel system, the refrigerant system of the vehicle, or even the tire inflation of the vehicle. The goal is to certify that the vehicle emissions are based only on the fueling system.

Such isolation of emission problems to specific systems are speeded further by the optional probes 101 or 102 placed at specific locations on the vehicle. These probes were used in the prior art in a manner which caused delay time due to the long paths to the sampling equipment. With the use of a single heated sampling conduit 173 for both sampling of the interior ambient air of the testing structure as well as from probes 101 and 102 under the control of their respective control valves, the sampling time delays are considerably diminished.

Figure 2:
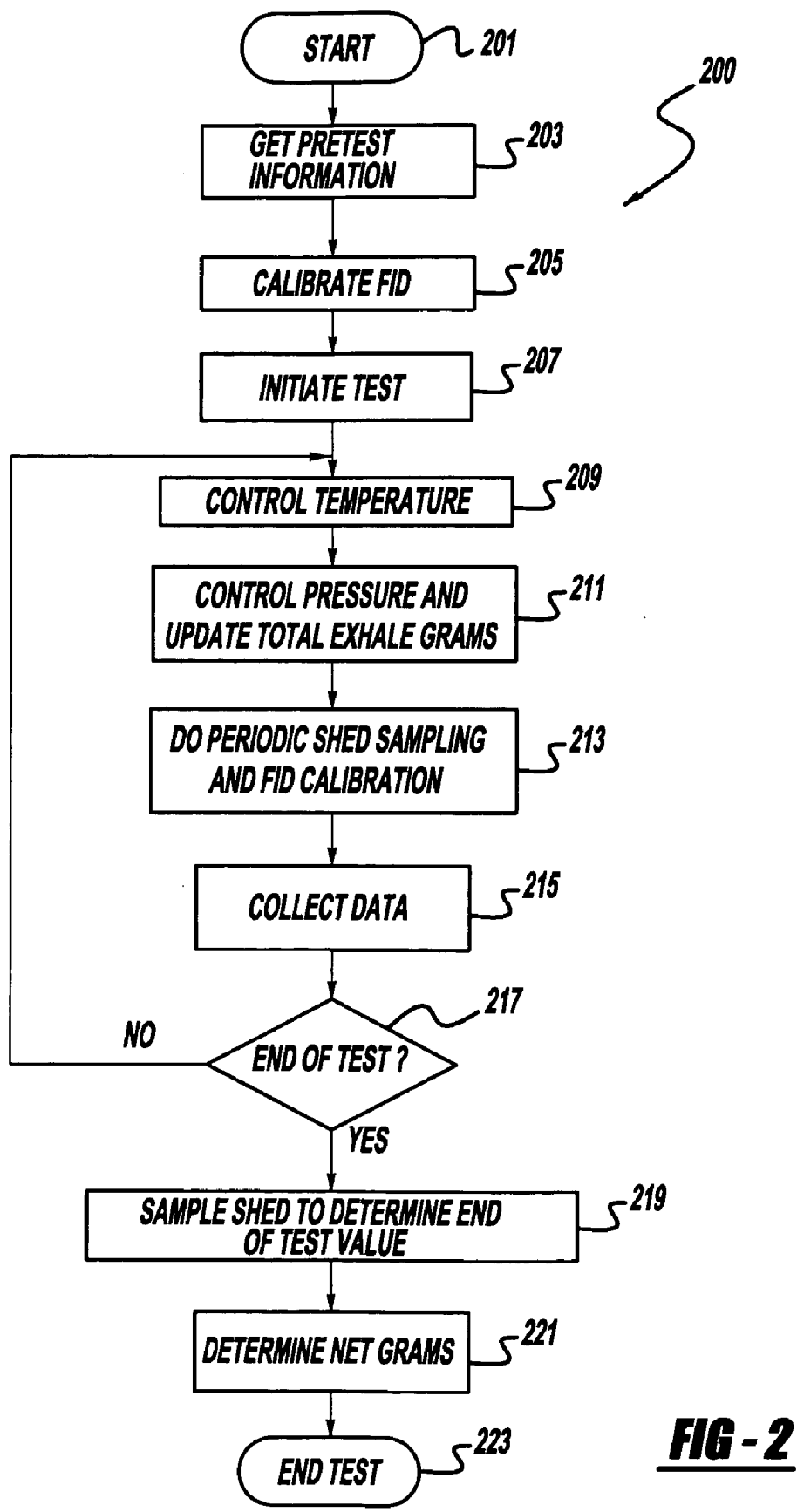
FIG. 2 is a flow chart of an exemplary method of determining evaporative vehicular emissions in accordance with the principles of the invention.

FIG. 2 sets forth a method 200 of conducting the evaporative testing with the apparatus described above in accordance with the principles of the invention. After starting the method at step 201, pretest information is gathered as step 203. Pre-test information may include, for example the test duration and the temperature profile to be used. Flame ionization detector 116 is then calibrated at step 205 in accordance with the known propane sources discussed previously. Next, at step 207 the test is initiated, wherein a vehicle under test is placed within the SHED interior and an initial air sample is taken to determine the hydrocarbon content and the component parts of such hydrocarbon content by units 116 and 127 of FIG. 1.

The temperature inside the testing structure is then controlled at step 209 in accordance with a preselected temperature profile by equipment not shown.

Pressure fluctuations within the testing structure which are initiated by temperature changes therewithin are controlled, and in accordance with periodic samples, the total grams of hydrocarbons exhaled due to the requirements of the pressure differential control are updated at step 211.

At step 213, air samples are periodically taken via heated sample line 173 and the flame ionization detector 116 is also periodically calibrated. Gas analyzer 127 is calibrated offline, and its periodic calibration is not a part of the overall method set forth in FIG. 2.

At step 215, the hydrocarbon and/or component part data are collected for each sample, and a running count of the emissions is maintained by controller 180 of FIG. 1.

At decision block 217, if the duration period which is a predefined time period has not expired, the routine loops back to step 209 to repeat steps 211–215. If the test duration has ended, an additional sample of the ambient air within the testing structure is taken to determine the final value of hydrocarbons and optionally the component parts thereof at step 219. At step 221, controller 180 determines the net grams of hydrocarbon that have been emitted by the vehicle during the test cycle, and the routine then ends at step 223.

Figure 3:
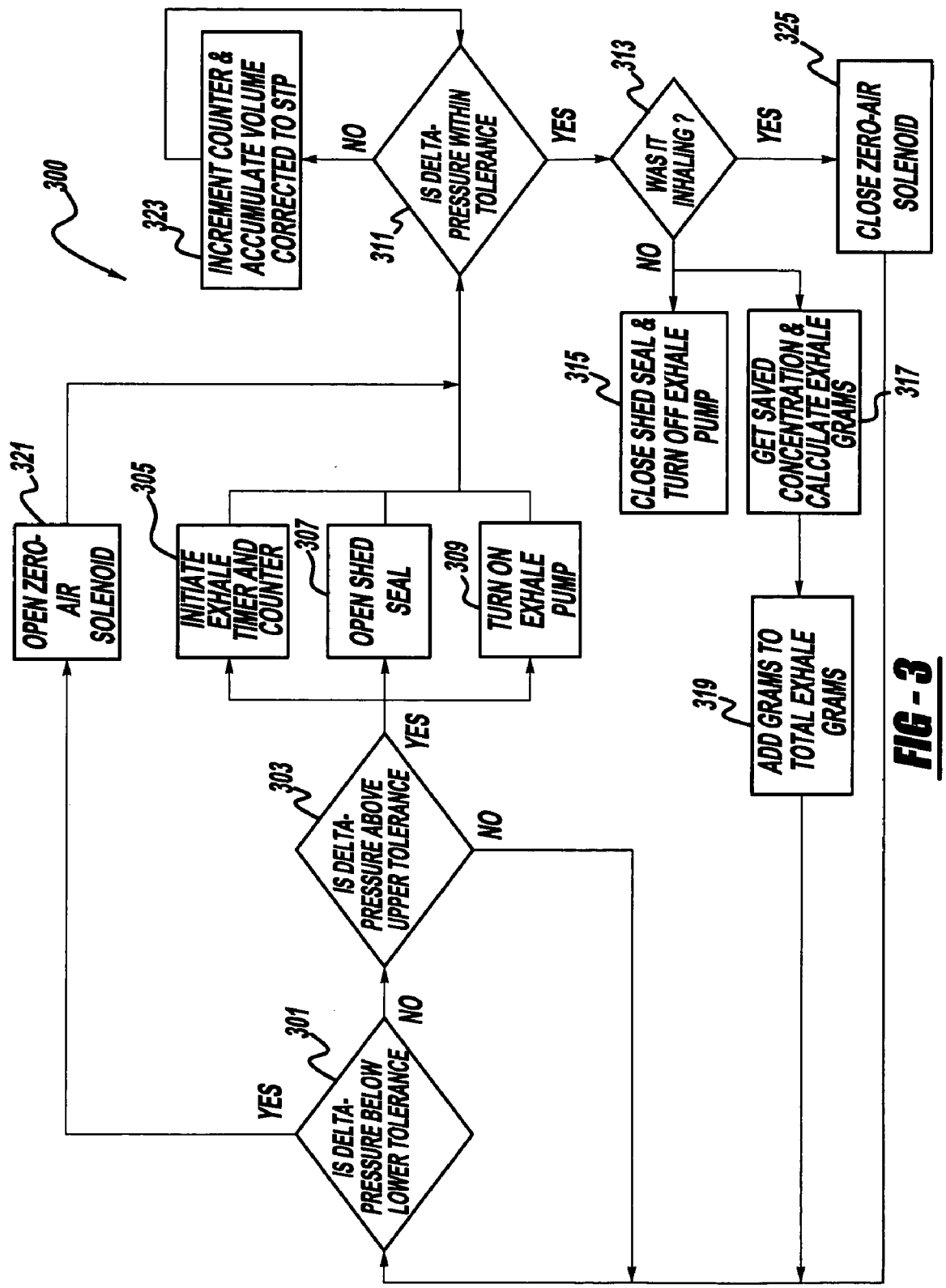
FIG. 3 is a flow chart showing further details of adjusting a total emission level to account for any withdrawal of ambient air from the testing structure of the invention.

FIG. 3 sets forth the method performed by controller 180 in monitoring the pressure differential between the outside atmosphere and the internal ambient air of the testing structure and for compensating the running total of emitted grams of hydrocarbons during the test interval.

This method 300 begins at decision block 301. If the pressure inside the testing structure is lower than the atmospheric pressure outside of the structure by a preselected tolerance, then the zero hydrocarbon air pathway of FIG. 1 is opened at step 321. If the pressure inside the testing structure is not below that of the outside atmosphere by a preselected tolerance, then the routine steps to decision block 303. In decision block 303, if the pressure of the ambient air within the testing structure is higher than the outside atmosphere by a preselected upper tolerance, then the SHED is allowed to exhale at step 307. If the pressure differential for both upper and lower tolerances has not been exceeded, then the routine loops back to decision block 301.

If the pressure of the internal ambient air of the testing structure exceeds the outside atmosphere by the preselected tolerance level, then an exhale timer and counter is initiated at step 305, the SHED outlet exhale port of FIG. 1 is opened at step 307 and simultaneously the exhale pump is turned on at step 309.

If the testing structure has zero hydrocarbon air injected at step 321 or if the exhale initiation steps of 305, 307 and 309 are initiated, then the routine enters decision block 311. Again, the pressure differential between the inside and outside of the testing structure is monitored and if it is within a tolerance level, the routine proceeds to decision block 313. If the pressure differential is not within tolerance, then controller 180 of FIG. 1 increments a counter for accumulating the total hydrocarbons being emitted within the testing structure, and the volume of emitted air is accumulated corrected to standard temperature and pressure (STP).

At decision block 313, controller 180 determines if the testing structure was inhaling (i.e. being injected with zero hydrocarbon air). If the testing structure was inhaling, then the zero air supply solenoid control valve is closed at step 325 and the routine returns to decision block 301.

If the testing structure was not inhaling at step 313, then it must have been exhaling. The SHED opening for exhaling is closed at step 315 and simultaneously at step 317 the amount of exhaled grams of hydrocarbons is calculated in accordance with the monitored flow rate and saved. At step 319, the exhaled hydrocarbon grams are added to the emission running count, and the routine returns to step 301.

In this manner, a running count of emitted hydrocarbons (and their constituent components) is maintained via periodic sampling through conduit 173 and, if the interior of the testing structure exhaled air to overcome pressure differentials, this running count is compensated by adding hydrocarbons which were bled off from the testing structure during the routine. By using substantially zero hydrocarbon containing air as an injector into the testing structure to raise the pressure therein, no compensation is required.

The invention has been described with reference to a preferred embodiment, for the sake of example. The scope and spirit of the invention are to be determined by appropriately interpreting the appended claims.

We claim:

1. A system for testing motor vehicle evaporative emissions comprising:

a substantially air-tight testing structure adapted for enclosing a motor vehicle to be placed under test, the testing structure containing a known volume of ambient interior air;

a sampling mechanism for periodically measuring and analyzing total hydrocarbon content and component parts of the total hydrocarbon content in a sample of the ambient interior air;

a pressure measuring mechanism for indicating a pressure differential between the ambient interior air and atmosphere outside of the testing structure;

an injector element for injecting air containing substantially zero hydrocarbons into the testing structure whenever the pressure of the atmosphere outside of the testing structure is higher than the pressure of the ambient interior air by a preselected differential;

an exhaling element for withdrawing interior ambient air from the testing structure whenever the pressure of the ambient interior air is higher than the pressure of the atmosphere outside of the testing structure by a redetermined differential;

a flow measuring and calculation element for determining, in conjunction with a most recent sample from the sampling mechanism, an amount of hydrocarbons exhaled from the testing structure whenever the exhaling element is withdrawing interior ambient air from the testing structure; and a hydrocarbon source coupled to an interior of the testing structure via a gravimetric injection device.

2. The system of claim 1, further comprising:

at least one air sampling probe positioned at a predetermined location on the vehicle within the testing structure, the at least one probe selectively coupled to the sampling mechanism.

3. The system of claim 1, wherein the sampling mechanism further comprises:

a sampling conduit having a first end selectively coupled to an interior of the testing structure;

a gas analyzer selectively coupled to a second end of the sampling conduit for determining component parts of the hydrocarbons in the sample; and a flame ionization detector selectively coupled to the second end of the sampling conduit for measuring total hydrocarbon content in the sample.

4. The system of claim 3, further comprising:

a calibration system operative to couple a source of calibration gas containing a known amount of hydrocarbon to the first end of the sampling conduit to calibrate the flame ionization detector while compensating for any contamination in the sampling conduit.

5. The system of claim 4, wherein the source of calibration gas is coupled to the first end of the sampling conduit via a valve spill-over arrangement.

6. The system of claim 3 wherein the gas analyzer comprises a photo acoustic gas analyzer.

7. The system of claim 1, wherein the flow measuring and calculation element includes a laminar flow element and a pressure transducer coupled to opposite ends of the laminar flow element.

8. The system of claim 1, wherein the testing structure encloses a practically zero emission vehicle.

9. The system of claim 3, wherein the sampling conduit is heated.

10. A method for determining evaporative emissions of a motor vehicle over a predetermined test time interval, the method comprising:

enclosing a subject motor vehicle in a substantially airtight testing structure containing a known volume of ambient interior air;

periodically sampling during the test time interval the ambient interior air for hydrocarbon content and maintaining a running count of the hydrocarbon content;

monitoring a pressure differential between the ambient interior air and atmosphere outside of the testing structure;

injecting air containing substantially zero hydrocarbons into the testing structure whenever the pressure differential indicates atmospheric pressure outside the testing structure exceed internal ambient air pressure by a preselected amount;

withdrawing interior ambient air from the testing structure whenever the pressure differential indicates interior ambient air pressure exceeds atmospheric pressure outside the testing structure by a preselected amount; and determining an amount of hydrocarbons withdrawn from the testing structure for any withdrawal of interior ambient air and adjusting the running count accordingly; and periodically sampling air containing a known amount of hydrocarbons for calibration purposes using a hydrocarbon source coupled to an interior of the testing structure via a gravimetric injection device.

11. The method of claim 10, further comprising determining, during sampling, amounts of preselected components of the hydrocarbon content.

12. The method of claim 11, wherein amounts of preselected components of the hydrocarbon content are determined by using a photo acoustic gas analyzer.

13. The method of claim 10, wherein the amount of hydrocarbons withdrawn is determined by deriving a flow rate of any ambient air exiting the testing structure.

14. The method of claim 13, wherein the flow rate of the ambient air exiting the testing structure is derived by monitoring a pressure differential across a laminar flow element positioned within the testing structure.

* * * * *